US012623062B2

(12) United States Patent
Reynolds et al.

(10) Patent No.: US 12,623,062 B2
(45) Date of Patent: May 12, 2026

(54) RADIAL ACCESS BALLOON CATHETER

(71) Applicant: Surmodics MD, LLC, Eden Prairie, MN (US)

(72) Inventors: Michael Reynolds, Galway (IE); Simon Davis, Galway (IE)

(73) Assignee: Surmodics MD, LLC, Eden Prairie, MN (US)

( * ) Notice: Subject to any disclaimer, the term of this patent is extended or adjusted under 35 U.S.C. 154(b) by 695 days.

(21) Appl. No.: 17/901,165

(22) Filed: Sep. 1, 2022

(65) Prior Publication Data

US 2023/0071144 A1 Mar. 9, 2023

Related U.S. Application Data

(60) Provisional application No. 63/239,717, filed on Sep. 1, 2021.

(51) Int. Cl.
A61M 25/10 (2013.01)
A61M 25/00 (2006.01)

(52) U.S. Cl.
CPC .... A61M 25/1025 (2013.01); A61M 25/0054 (2013.01)

(58) Field of Classification Search
CPC .......... A61M 25/0052; A61M 25/0053; A61M 25/0054; A61M 25/0169; A61M 25/0172; A61M 2025/0183; A61M 25/1025
See application file for complete search history.

(56) References Cited

U.S. PATENT DOCUMENTS

| | | | |
|---|---|---|---|
| 4,170,996 A | 10/1979 | Wu | |
| 4,921,482 A | 5/1990 | Hammerslag et al. | |
| 5,060,660 A | 10/1991 | Gambale et al. | |
| 5,203,772 A | 4/1993 | Hammerslag et al. | |
| 5,449,343 A | 9/1995 | Samson et al. | |
| 5,549,552 A | 8/1996 | Peters et al. | |
| 6,071,273 A * | 6/2000 | Euteneuer | A61M 25/0029 604/533 |
| 6,152,912 A | 11/2000 | Jansen et al. | |
| 6,228,073 B1 | 5/2001 | Noone et al. | |

(Continued)

FOREIGN PATENT DOCUMENTS

| | | |
|---|---|---|
| CN | 101479006 | 7/2009 |
| CN | 101588835 | 11/2009 |

(Continued)

OTHER PUBLICATIONS

"U.S. Appl. No. 17/234,206, Corrected Notice of Allowability mailed Sep. 7, 2023", 2 pgs.

(Continued)

*Primary Examiner* — Cris L. Rodriguez
(74) *Attorney, Agent, or Firm* — Schwegman Lundberg & Woessner, P.A.

(57) ABSTRACT

Discussed herein are various embodiments related to a catheter assembly. The catheter assembly can include a catheter body extending between a proximal portion and a distal portion. The catheter body can include a sleeve and a hypotube, connected by at least one bond site, and separated by a floating gap. The hypotube can include at least one flow opening extending from the hypotube lumen to a stagnation zone, configured to permit flow between the stagnation zone and the hypotube lumen.

29 Claims, 7 Drawing Sheets

(56) References Cited

U.S. PATENT DOCUMENTS

| | | | |
|---|---|---|---|
| 6,595,989 | B1 | 7/2003 | Schaer |
| 6,626,889 | B1 | 9/2003 | Simpson et al. |
| 6,676,643 | B2 | 1/2004 | Brushey |
| 6,702,782 | B2 | 3/2004 | Miller et al. |
| 6,761,703 | B2 | 7/2004 | Miller et al. |
| 7,070,606 | B2 | 7/2006 | Seward |
| 7,115,134 | B2 | 10/2006 | Chambers |
| 7,115,183 | B2 | 10/2006 | Larson et al. |
| 7,166,100 | B2 | 1/2007 | Jordan et al. |
| 7,247,147 | B2* | 7/2007 | Nishide ............... A61M 25/104 604/103.1 |
| 7,309,334 | B2 | 12/2007 | von Hoffmann |
| 7,632,242 | B2* | 12/2009 | Griffin .............. A61M 25/1002 604/102.03 |
| 7,708,704 | B2 | 5/2010 | Mitelberg et al. |
| 7,708,755 | B2 | 5/2010 | Davis, III et al. |
| 7,785,317 | B2 | 8/2010 | Mitelberg |
| 7,815,600 | B2 | 10/2010 | Al-Marashi et al. |
| 8,012,117 | B2 | 9/2011 | Bonnette et al. |
| 8,021,351 | B2 | 9/2011 | Boldenow et al. |
| 8,088,121 | B2* | 1/2012 | Nishide ............. A61M 25/1006 604/524 |
| 8,317,715 | B2 | 11/2012 | Belleville et al. |
| 8,323,203 | B2 | 12/2012 | Thornton |
| 8,337,518 | B2 | 12/2012 | Nance et al. |
| 8,454,673 | B2 | 6/2013 | Al-Marashi et al. |
| 8,523,841 | B2 | 9/2013 | Itou et al. |
| 8,585,713 | B2 | 11/2013 | Ferrera et al. |
| 8,728,116 | B1 | 5/2014 | Janardhan et al. |
| 8,758,334 | B2 | 6/2014 | Coe et al. |
| 8,771,329 | B2 | 7/2014 | Christensen et al. |
| 8,939,931 | B2 | 1/2015 | Von Hoffmann |
| 9,005,165 | B2 | 4/2015 | Kalser et al. |
| 9,060,784 | B2 | 6/2015 | Coe et al. |
| 9,179,995 | B2 | 11/2015 | Janardhan et al. |
| 9,289,576 | B2* | 3/2016 | Mann ................ A61M 25/0054 |
| 9,301,777 | B2 | 4/2016 | Silvestro |
| 9,339,632 | B2* | 5/2016 | Eidenschink ........... A61L 29/02 |
| 9,372,217 | B2 | 6/2016 | Hahl et al. |
| 9,445,784 | B2 | 9/2016 | O'Keeffe |
| 9,616,195 | B2 | 4/2017 | Lippert et al. |
| 9,636,173 | B2 | 5/2017 | Goshgarian et al. |
| 9,692,557 | B2 | 6/2017 | Murphy |
| 9,833,125 | B2 | 12/2017 | Stigall et al. |
| 9,861,727 | B2 | 1/2018 | Slager et al. |
| 9,955,852 | B2 | 5/2018 | Kesten et al. |
| 10,292,573 | B2 | 5/2019 | Stigall et al. |
| 10,315,018 | B2 | 6/2019 | Eidenschink et al. |
| 10,363,389 | B2 | 7/2019 | Lippert et al. |
| 10,434,292 | B2 | 10/2019 | Joe et al. |
| 10,449,334 | B2 | 10/2019 | Pillai |
| 10,561,820 | B2 | 2/2020 | Sullivan et al. |
| 10,568,991 | B2 | 2/2020 | Wang et al. |
| 10,617,847 | B2 | 4/2020 | Cottone et al. |
| 10,687,690 | B2 | 6/2020 | Kesten et al. |
| 10,688,277 | B2 | 6/2020 | O'Connell et al. |
| 10,709,312 | B2 | 7/2020 | Stigall et al. |
| 10,980,918 | B2 | 4/2021 | Babcock et al. |
| 11,000,632 | B2 | 5/2021 | Babcock et al. |
| 11,865,237 | B2 | 1/2024 | Davis et al. |
| 2001/0049519 | A1 | 12/2001 | Holman et al. |
| 2002/0007146 | A1* | 1/2002 | Omaleki ................ A61M 25/09 604/103.09 |
| 2003/0083691 | A1* | 5/2003 | Wantink ............ A61M 25/0052 604/103.04 |
| 2005/0075661 | A1 | 4/2005 | Levine et al. |
| 2005/0267408 | A1* | 12/2005 | Grandt .............. A61M 25/0029 604/103.04 |
| 2006/0264904 | A1 | 11/2006 | Kerby et al. |
| 2007/0016133 | A1* | 1/2007 | Pepper .............. A61M 25/0052 604/103.04 |
| 2007/0060880 | A1 | 3/2007 | Gregorich et al. |
| 2007/0073331 | A1 | 3/2007 | Brown et al. |
| 2008/0077085 | A1 | 3/2008 | Eidenschink et al. |

| | | | |
|---|---|---|---|
| 2008/0306441 | A1 | 12/2008 | Brown et al. |
| 2011/0319905 | A1 | 12/2011 | Palme et al. |
| 2012/0303054 | A1 | 11/2012 | Wilson et al. |
| 2014/0193474 | A1 | 7/2014 | Babcock et al. |
| 2014/0358074 | A1* | 12/2014 | Wilson ................ A61M 25/104 604/96.01 |
| 2015/0258307 | A1 | 9/2015 | Osypka et al. |
| 2015/0305867 | A1 | 10/2015 | Liu et al. |
| 2015/0374483 | A1 | 12/2015 | Janardhan et al. |
| 2016/0339207 | A1 | 11/2016 | Beeckler et al. |
| 2017/0165001 | A1 | 6/2017 | Lyttle |
| 2017/0296221 | A1 | 10/2017 | Di Caprio et al. |
| 2018/0042743 | A1 | 2/2018 | Syed |
| 2018/0153669 | A1 | 6/2018 | Herrera et al. |
| 2018/0250147 | A1 | 9/2018 | Syed |
| 2019/0083757 | A1 | 3/2019 | Torres et al. |
| 2019/0275260 | A1 | 9/2019 | Ralph et al. |
| 2019/0298520 | A1 | 10/2019 | Cooper et al. |
| 2020/0016378 | A1 | 1/2020 | Williams et al. |
| 2020/0023164 | A1 | 1/2020 | Tran et al. |
| 2020/0060723 | A1 | 2/2020 | Walzman |
| 2020/0078551 | A1 | 3/2020 | Moquin et al. |
| 2020/0078554 | A1 | 3/2020 | Walzman |
| 2020/0222664 | A1 | 7/2020 | Cottone et al. |
| 2020/0230359 | A1 | 7/2020 | Fojtik et al. |
| 2021/0322732 | A1 | 10/2021 | Davis |
| 2024/0157097 | A1 | 5/2024 | Davis et al. |

FOREIGN PATENT DOCUMENTS

| | | |
|---|---|---|
| CN | 106166067 | 11/2016 |
| CN | 108211084 | 6/2018 |
| CN | 110236600 | 9/2019 |
| CN | 115666699 | 1/2023 |
| JP | 2018099521 | 6/2018 |
| JP | 2019071914 | 5/2019 |
| JP | 2023522978 | 6/2023 |
| WO | WO-2021216442 A1 | 10/2021 |
| WO | 2023034492 | 3/2023 |

OTHER PUBLICATIONS

"U.S. Appl. No. 17/234,206, Corrected Notice of Allowability mailed Dec. 6, 2023", 2 pgs.

"U.S. Appl. No. 17/234,206, Notice of Allowance mailed Aug. 23, 2023", 7 pgs.

"U.S. Appl. No. 18/516,464, Preliminary Amendment filed Feb. 6, 2024", 7 pgs.

"European Application Serial No. 21793660.8, Extended European Search Report mailed Jan. 23, 2024", 13 pgs.

"European Application Serial No. 21793660.8, Partial Supplementary European Search Report mailed Oct. 19, 2023", 13 pgs.

"International Application Serial No. PCT/US2021/027947, International Search Report mailed Aug. 3, 2021", 2 pgs.

"International Application Serial No. PCT/US2021/027947, Written Opinion mailed Aug. 3, 2021", 7 pgs.

"International Application Serial No. PCT US2022 042326, International Preliminary Report on Patentability mailed Mar. 14, 2024", 7 pgs.

"European Application Serial No. 21793660.8, Response filed Jul. 31, 2024 to Extended European Search Report mailed Jan. 23, 2024", 14 pgs.

"U.S. Appl. No. 18/516,464, Non Final Office Action mailed Oct. 1, 2024", 13 pgs.

"European Application Serial No. 22865553.6, Extended European Search Report mailed Dec. 2, 2024", 10 pgs.

"International Application Serial No. PCT US2021 027947, International Preliminary Report on Patentability mailed Nov. 3, 2022", 9 pgs.

"International Application Serial No. PCT US2022 042326, International Search Report mailed Dec. 22, 2022", 2 pgs.

"International Application Serial No. PCT US2022 042326, Written Opinion mailed Dec. 22, 2022", 5 pgs.

"U.S. Appl. No. 17/234,206, Non Final Office Action mailed Jan. 31, 2023", 11 pgs.

(56)               References Cited

OTHER PUBLICATIONS

"U.S. Appl. No. 17/234,206, Response filed May 1, 2023 to Non Final Office Action mailed Jan. 31, 2023", 13 pgs.
"U.S. Appl. No. 17/234,206, Examiner Interview Summary mailed May 3, 2023", 2 pgs.
"U.S. Appl. No. 18/516,464, Response filed Jan. 2, 2025 to Non Final Office Action mailed Oct. 1, 2024", 13 pgs.
"Japanese Application Serial No. 2022-564224, Notification of Reasons for Rejection mailed Feb. 12, 2025", W English Translation, 13 pgs.
"U.S. Appl. No. 18/516,464, Final Office Action mailed Mar. 31, 2025", 12 pgs.
"Chinese Application Serial No. 202180036481.X, Office Action mailed Mar. 26, 2025", W English Translation, 17 pgs.
"European Application Serial No. 22865553.6, Response filed Jun. 19, 2025 to Extended European Search Report mailed Dec. 2, 2024", w English Claims, 25 pgs.
"U.S. Appl. No. 18/516,464, Response filed Jun. 30, 2025 to Final Office Action mailed Mar. 31, 2025", 11 pgs.
"Japanese Application Serial No. 2022-564224, Response filed Jul. 2, 2025 to Notification of Reasons for Rejection mailed Feb. 12, 2025", w English Claims, 12 pgs.
"U.S. Appl. No. 18/516,464, Advisory Action mailed Jul. 22, 2025", 3 pgs.
"Chinese Application Serial No. 202180036481.X, Response filed Jul. 28, 2025 to Office Action mailed Mar. 26, 2025", W English Claims, 35 pgs.
"U.S. Appl. No. 18/516,464, Response filed Sep. 30, 2025 to Advisory Action mailed Jul. 22, 2025", 11 pgs.
"Chinese Application Serial No. 202180036481.X, Office Action mailed Oct. 14, 2025", W English Translation, 11 pgs.
"Japanese Application Serial No. 2022-564224, Examiners Decision of Final Refusal mailed Oct. 28, 2025", W English Translation, 9 pgs.
"U.S. Appl. No. 18/516,464, Advisory Action mailed Nov. 6, 2025", 3 pgs.
"U.S. Appl. No. 18/516,464, Non Final Office Action mailed Dec. 5, 2025", 15 pgs.
"Chinese Application Serial No. 202180036481.X, Response filed Dec. 15, 2025 to Office Action mailed Oct. 14, 2025", w/English Claims, 9 pgs.
"Japanese Application Serial No. 2022-564224, Response filed Feb. 27, 2026 to Examiners Decision of Final Refusal mailed Oct. 28, 2025", w/ English claims, 16 pgs.

* cited by examiner

RADIAL ACCESS BALLOON CATHETER

PRIORITY APPLICATION

This application claims the benefit of priority to U.S. Provisional Patent Application Ser. No. 63/239,717, filed Sep. 1, 2021, the content of which is incorporated by reference in its entirety.

TECHNICAL FIELD

This document pertains generally, but not by way of limitation, to catheter assemblies, or more particularly, to balloon catheters.

BACKGROUND

Catheters are used in a variety of medical procedures to conduct therapeutic or diagnostic functions within a patient. For instance, catheters are used for delivery of medications fluids or other therapies to specified locations in the patient. In other examples catheters conduct diagnostic procedures, withdraw fluids for testing, or drain fluids from the patient.

Balloon catheters are a variety of catheter. In some examples, a balloon catheter includes an elongated shaft with an inflatable balloon proximate to an end of the shaft. In use, the catheter is inserted and advanced, for instance with a guidewire to position the balloon at a location for treatment (e.g., a diseased vessel). The balloon and the catheter are filled with an inflation fluid in preparation for inflation of the balloon. Once inserted, the balloon is expanded with the inflation fluid to dilate a restriction, for instance a narrow opening or passage within a body. The fluid flows down the length of the catheter assembly to the balloon during inflation.

Dilation catheters treat vascular stenosis by inflating a balloon at a distal end of the catheter within the stenoses portion of the blood vessel to mechanically expand the blood vessel and restore blood flow. The catheter is inserted into the vascular system through an access site and navigated through the vasculature to reach the stenoses blood vessel. The access site is typically in the groin region due to close proximity and easy navigation to commonly stenosed regions of the vasculature such as the lower extremities and the coronary region. While groin access sites can simplify the procedure itself, the groin access site can present significant post-operation challenges. In particular, groin access sites are more likely to bleed uncontrollably and require an overnight hospital stay.

SUMMARY

The device being patented is a "radial access" balloon dilation catheter that can be navigated from a radial access site in the wrist or arm to reach stenosed regions throughout the body including in the lower extremities. In order to reach from the access point to the treatment sites, the radial access catheter is much longer than conventional dilation catheters (about 250 cm vs about 100 cm in length), which presents a number of challenges unique to these devices. The primary challenge is maintaining sufficient stiffness at the distal end of the catheter for easy navigation of the catheter through the vasculature while having sufficient flexibility to navigate tight bends in the vasculature. The "floating" spiral-cut hypotube design is intended to address these challenges by providing sufficient axial stiffness to allow easy navigation, while allowing extra flexibility to permit navigation of tight bends. The floating hypotube is fixed to the outer shaft of the catheter at the proximal end and at a mid-point of the shaft, while the remainder of the hypotube is allowed to "float" within the outer shaft. The floating construction allows the outer shaft to deflect further than the stiffer hypotube thereby allowing a higher effective bend radius for the catheter shaft.

The present inventors have recognized, among other things, that a problem to be solved can include regulating fluid flow through balloon catheters.

In order to provide a "floating" hypotube, the hypotube is attached to the outer shaft at the proximal end and at a mid-point while the regions between the attachment points and the distal end of the hypotube "float" within the outer shaft. This construction creates can be provide challenges when flushing or inflating/deflating the dilation catheter. Prior to insertion of the dilation catheter into the body, the catheter shaft is flushed with a saline solution to force air from the catheter shaft and test inflation of the balloon. The fluid is fed into the catheter through the hub at the proximal end of the catheter and passes through the hypotube exiting through the distal end of the hypotube before continuing to the distal end of the catheter. As the distal end of the catheter is not fixed to the outer shaft, air can become trapped in the "floating" region between the distal end of the hypotube and the midpoint attachment point of the shaft to the hypotube. This "stagnation zone" can likewise hinder deflation of the catheter as fluid is withdrawn from the catheter through the hypotube.

The balloon of a balloon catheter is inflated or deflated by movement of fluid along the length of the catheter body. Such a catheter assembly includes in some examples a sleeve (such as an outer liner), a hypotube at least partially within the sleeve, the hypotube having a hypotube lumen, and a balloon coupled with sleeve of the catheter body. The inflation fluid, such as a liquid, is pushed distally along the lumen of the hypotube toward the balloon to initiate inflation. The fluid is moved proximally along the catheter assembly, such as along the hypotube lumen, to deflate the balloon.

During inflation and deflation, or other times fluid is pushed down the catheter body, fluid flow can occur between the hypotube and the outer sleeve in the catheter body. The hypotube and sleeve can be bonded to each other at a number of points along the catheter body. Often, in a portion of the catheter body distal of bond sites between the hypotube and the outer sleeve, fluid flow can stagnate, build-up, or stop, causing a "stagnation zone". In some cases, bubbles or pockets of gas are trapped between the liquid at this stagnation zone. For example, this can occur during inflation or deflation of the balloon, where liquid is flowing through the hypotube and in a floating gap between the hypotube and the interior wall of the outer sleeve.

Priming or evacuation of the catheter are in some examples conducted to minimize trapping of gas within stagnation zones. Similarly, evacuation is conducted to minimize trapping of inflation fluid within stagnation zones. In some examples priming and evacuation are repeated in numerous instances in an attempt to fully withdraw trapped gas or inflation fluid. The repeated priming and evacuation procedures are lengthy and labor intensive, and in various examples may fail to fully evacuate the trapped gas or inflation fluid.

The present subject matter provides solutions to these problems with a hypotube including flow openings. The flow openings can be situated in the hypotube wall distal of bond sites between the hypotube and the outer sleeve of the catheter assembly. The flow openings can allow for fluid movement in a zone or area that can be prone to stagnation.

Examples of a long, soft catheter that is both flexible and pushable are described herein. In one example, the catheter assembly can include a hypotube and a sleeve, moveable relative each other, and an inflatable balloon on the distal portion of the assembly. The hypotube and the sleeve can be bonded to each other at one or more bond points along the length of the assembly. The hypotube, for placement at least partially within the sleeve, can include a spiral cut. Discussed herein, such a catheter can include flow openings proximal of the spiral cut on the hypotube, and distal of at least one of the bond points. The openings can allow for more efficient flushing, inflation and deflation of the balloon.

In another example, a catheter assembly can include a catheter body extending between a proximal portion and a distal portion. The catheter body can include a hypotube, flow openings, and a sleeve. The hypotube can extend between the proximal and distal portions, and the flow openings can reside on the hypotube in a stagnation zone. The sleeve can be coupled around the hypotube and extend between the proximal and distal portions. The sleeve can be spaced from the hypotube by a floating gap. The flow openings can allow flow between the hypotube and the floating gap in the stagnation zone.

In an example, the catheter assembly can further include a balloon fluidly attached to the distal portion of the catheter body. The balloon can be inflated and deflated by movement of fluid through the catheter body. The flow openings can allow for fluid flow through the stagnation zone when the balloon is being inflated or deflated.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The example catheter assemblies described herein allow for better fluid flow throughout the catheter body, such as between a catheter sleeve and hypotube. The hypotube can include flow openings to allow for fluid flow between the sleeve and hypotube, and reduce bubbles and stagnation between the two components.

An example catheter assembly that can be used with the methods discussed herein is described in application Ser. No. 17/234,206, incorporated herein by reference in its entirety.

In the example catheter assemblies discussed herein, there can be several distinct stiffness zones along the length of the assembly. The catheters discussed herein can, for example, from a proximal portion to a distal portion, include a stiff region to allow pushablity of the catheter assembly, a first spiral cut region that can provide more stiffness and less flexibility, a second spiral cut region that can provide more flexibility and less stiffness, and an unsupported, or floating, region that can provide more flexibility.

These different regions can provide a transition in stiffness to flexibility along the length of the catheter assembly 100 from the proximal portion 104 to the distal portion 106. The proximal portion 104 can be preferably stiffer to allow for easier control of the catheter assembly 100. In contrast, the distal portion 106 can be more flexible than the proximal portion 104 to allow for ease in navigation of the catheter assembly 100 through small, narrow or tortuous anatomy.

Figure 1:
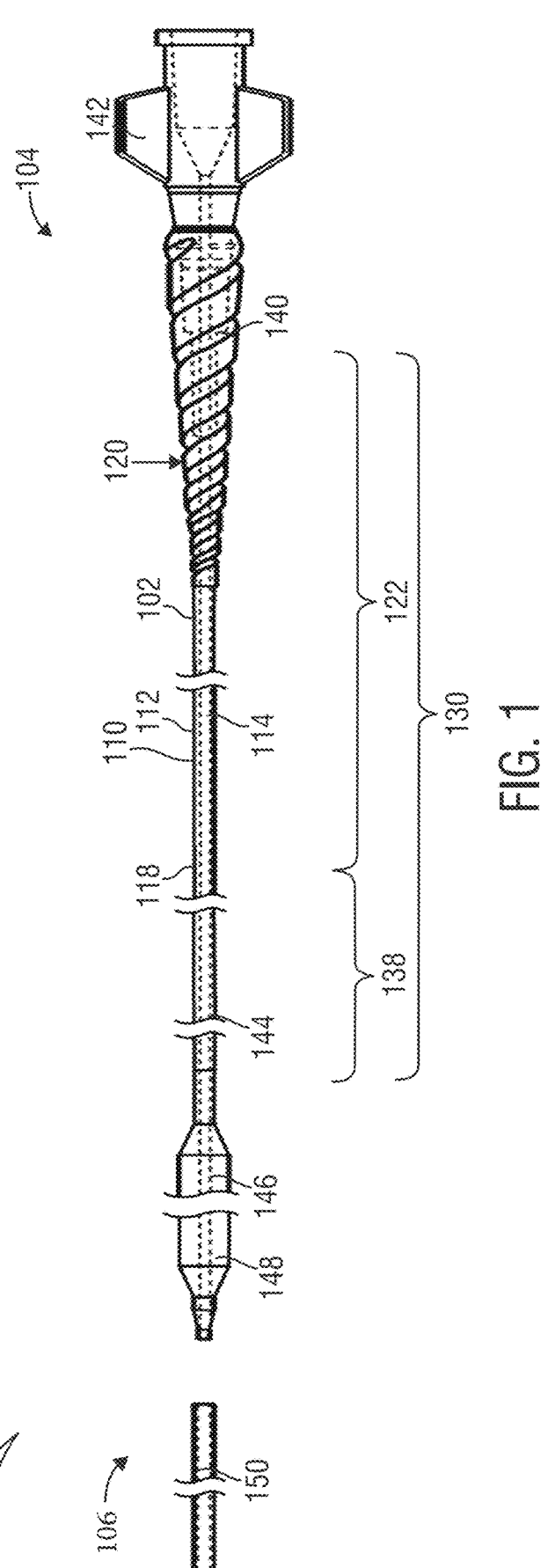
FIG. 1 is a side view of one example of a catheter assembly and a hypotube with flow openings.
Figure 2:
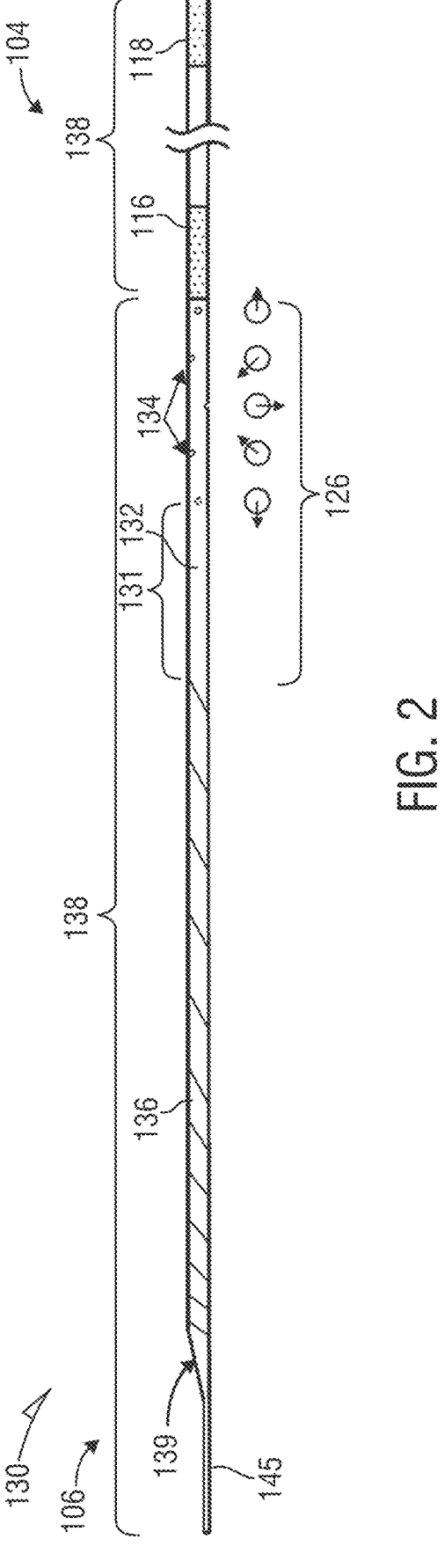
FIG. 2 is a side view of one example of a hypotube with flow openings, the hypotube for use with the catheter assembly of FIG. 1.
Figure 3:
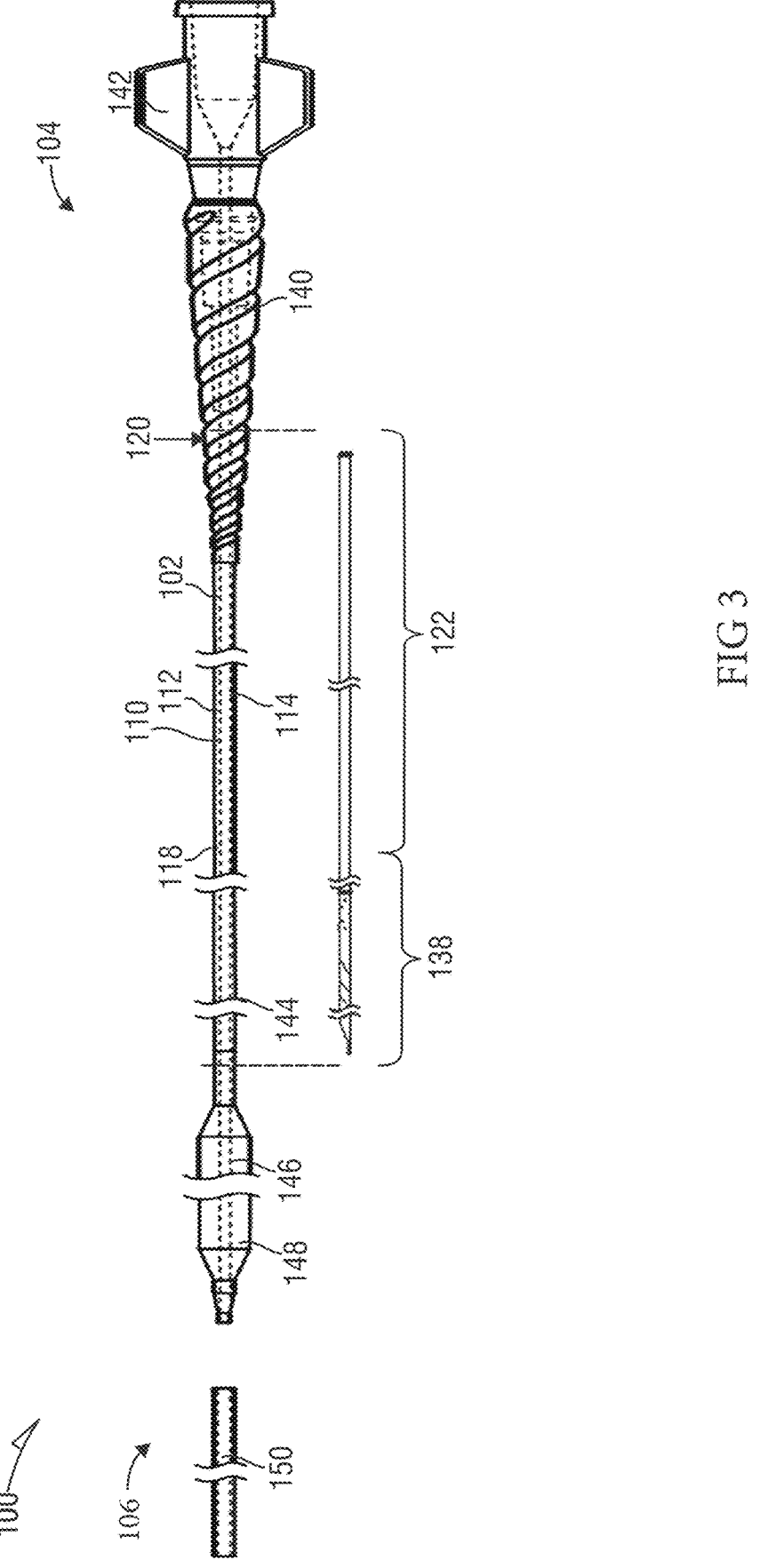
FIG. 3 is a disassembled configuration of the catheter body and hypotube of FIG. 1.

FIG. 1 illustrates a side view of one example of a catheter assembly 100, and FIG. 2 illustrates a side view of one example of a hypotube 130 with flow openings, the hypotube for use with the catheter assembly 100 of FIG. 1. FIG. 3 illustrates a side view of one example of the catheter assembly 100 with an external hypotube. FIGS. 1, 2, and 3 will be discussed together.

In the example catheter assembly 100, the floating segment 122 is an example of a stiff region, allowing pushability of the catheter assembly 100. Here, the hypotube 130 is not spiral cut, and is floating within a lumen 114. The first spiral cut region, which provides more stiffness and some flexibility, can be at a proximal portion of the hypotube 130, distal of the floating segment 122. Here, the spiral cut can be pitched to provide more stiffness than flexibility. This can serve, for example, as a transition region. The second spiral cut region, which provides more flexibility and some stiffness, can be at a distal portion of the hypotube 130. Here, the hypotube 130 can be spiral cut at an angle to allow for less stiffness and more flexibility, transitioning to the distal portion 106. At the distal portion 106, the unsupported region can be made of the balloon 146, the balloon protector 148, and the distal tip assembly 150. This can be flexible, and can be up to about 30 cm in length.

The catheter assembly 100 includes a catheter body 102 extending between a proximal portion 104 and a distal portion 106. The overall length of the catheter assembly 100 can be about 200 cm to about 250 cm. The catheter body 102 includes a sleeve 110 with a lumen 112 and a hypotube 130 with a lumen 132. The sleeve 110 and the hypotube 130 extend between the proximal portion 104 and the distal portion 106. The hypotube 130 can be situated within the sleeve 110. The hypotube and the sleeve define a floating gap 114 which can be situated between the hypotube 130 and the sleeve 110 at one or more segments of the catheter body 102. The hypotube 130 includes one or more flow openings 134, situated in or near a fluid stagnation zones 126 in the floating gap 114. The flow openings 134 can extend between the hypotube lumen 132 and the sleeve lumen 112 to allow fluid flow between the stagnation zone 126, and the hypotube lumen 132.

In example catheter assembly 100, the sleeve 110 is a "floating" sleeve, surrounding the hypotube 130. The floating sleeve 110 is, as described in examples herein, coupled with the hypotube 130 at one or more bond sites while otherwise including floating segments that permit relative movement between the floating sleeve 110 and the hypotube 130. In FIG. 1 the catheter assembly 100 includes a proximal bond site 120 and distal bond site 118. One or more floating segments are interposed between the bond sites. For instance, the floating hypotube segment 122 is interposed between the proximal and middle bond sites 118, 120. Portions of the hypotube 130, such as those adjacent bond sites, can be subject to fluid flow stagnation, such as stagnation zone 126, distal of bond sites 118, 120, respectively. The floating segment 122 can be non-spiral cut. This can allow for the floating segment 122 to help increase pushability of the catheter assembly 100. Here, the hypotube 130 can float within the outer shaft of this region. This is illustrated, for example, at FIG. 4 below, with reference to the proximal portion 404 and the region 426.

Referring now to FIG. 2, the hypotube 130 of the catheter assembly 100 extends between a hypotube proximal portion 104 and a hypotube distal portion 106, such as within a lumen of the sleeve 110. In one example, the distal portion 106 of the hypotube 130 includes an end portion 145 having a skive 139 (e.g., a tapered edge for easier insertion and guiding of the catheter). The hypotube 130 in this example includes one or more helical grooves 136 at a spiral cut region 138 (e.g., cuts, scoring, perforations or the like). For instance, the helical grooves 136 can include one or more pitch angles, pitch widths, or the like to provide specified mechanical characteristics to the various portions of the hypotube 130 and corresponding characteristics to the catheter assembly 100. The spiral cuts can be at a constant pitch to balance support and flexibility, such as near the proximal portion 104. Near the distal portion 106, the spiral cuts can decrease in pitch, to allow for flexibility at the distal portion 106. Such flexibility may be useful for navigation of the catheter assembly 100 in tortuous regions.

Referring again to FIG. 1, the example catheter assembly 100 further includes a strain relief portion 140 and a hub 142. The catheter body 102 of the catheter assembly 100 extends distally from the hub 142 (e.g., through the strain relief portion 140) to the distal portion 106. The catheter assembly 100 optionally includes an access port 144 for rapid exchange delivery of the catheter assembly 100. In the example shown in FIG. 1 the present catheter body includes a balloon 146, a balloon protector 148, and a distal tip assembly 150, such as an atraumatic tip. The catheter assembly 100 extends between the proximal portion 104 and the distal portion 106 with the strain relief portion 140 proximate to the proximal portion 104 and the hub 142.

In the example shown in FIG. 1 the floating sleeve 110 receives the hypotube 130 therein. The floating sleeve 110 includes one or more floating regions joined by the bond sites. The floating sleeve optionally includes a floating segment (e.g., decoupled from the hypotube 130) that extends from the proximal portion 104 to the distal portion 106. In another example including the bond sites 118 and 120, the floating sleeve 110 includes the floating segment 122 between the bond sites 118, 120. The bond sites 118, 120 secures the floating sleeve 110 to the hypotube 130 while the remainder of the floating sleeve 110 is decoupled from the hypotube 130 as described herein. In an example including the access port, the access port 144 is proximate to the distal portion 106, for instance near the distal bond site 120. Near the bond sites 118, 120, such as at floating segment 122, stagnation of fluid flow can occur, causing one or more stagnation zones 126, 128.

The catheter assembly 100 may be, for example, a catheter for drainage, administration of fluids or gases, access by surgical instruments, or to perform a variety of other procedures depending on the desired outcome. In one example, the catheter body 102 of the assembly 100 has a length of between about 2.0 m to about 4.0 m. The catheter body 102, as described herein, is a component of the catheter assembly 100 having the hub 142 and one or more instruments, catheter instruments, guide catheters, introducers or the like that are delivered through vessels and cavities of a patient, for instance from the leg to the heart or from the wrist to the heart. As described herein the catheter assembly 100 and variations of the same allow for fluid flow between the sleeve 110 and the hypotube 130, and overall reduced fluid stagnation.

The catheter assembly 100 optionally includes a biocompatible coating thereon, such as a hydrophilic coating on an outer surface of the catheter body 102 or the floating sleeve 110 for ease of insertion. The coating can be, for example, a drug coating or a hydrophilic lubricious coating, such as described in U.S. patent publication 2014/0193474 and U.S. Pat. No. 10,980,918, which are herein incorporated by reference.

The floating sleeve 110, and outer body, is an outer jacket-like structure in the catheter assembly 100 coupled around the hypotube 130 (e.g., covering, partially covering, surrounding, or partially surrounding). The floating sleeve 110 need not be attached to the hypotube 130. In an example, there is clearance between the floating sleeve 110 and the hypotube 130 to permit relative movement of the hypotube 130 and the floating sleeve 110. The floating sleeve 110 optionally includes multiple floating segments alternating with bond sites. For example, in FIG. 1, one floating hypotube segment 122 is shown, interspersed with two bond sites: bond site 118 and bond site 120. The floating sleeve 110 and the bond sites 118, 120 are interconnected with hypotube 130 to permit relative movement of the one or more floating segments of the sleeve 110 relative to the hypotube 130.

The one or more bond sites are positioned within the catheter assembly 100 to allow attachment of the floating sleeve 110 at specified locations along the catheter assembly 100. The one or more bond sites secure, fasten, or anchor the floating sleeve 110 to the corresponding portion (or portions) of the hypotube 130. In FIG. 1, the proximal bond site 120 is optionally positioned beneath the strain relief portion 140, for instance between the floating sleeve 110 and the hypotube 130. The bond sites fix the proximate portions of the sleeve 110 and the hypotube 130 at least against relative longitudinal motion in at least one direction (e.g., proximally, distally or both). For example, each bond site of the catheter assembly 100 constrains longitudinal motion proximate to the bond site in at least one degree of freedom between the floating sleeve 110 and the hypotube 130 (e.g., permits unidirectional longitudinal motion while restricting longitudinal motion in a converse direction, or constrains longitudinal motion in multiple directions).

The distal bond site 120 is between the floating sleeve 110 and the hypotube 130 on or near the distal portion 106 of the catheter assembly 100. In the example shown in FIG. 1, the distal bond site 120 is proximate the access port 144, such as a rapid exchange access port. A rapid exchange port can permit the use of shorter guidewires in conjunction with the catheter assembly 100. This can allow for the use of guidewires that are shorter than the overall length of the catheter assembly 100. In this case, the guidewire can enter from a mid-point of the catheter assembly 100, instead of through the proximal portion 104 or the distal portion 106. In some cases, the distal bond site 120 secures (e.g., fastens, anchors or the like) the proximate portion of the hypotube 130 to the corresponding portion of the floating sleeve 110. Optionally, the distal bond site 120 is integrated with the access port 144. In one example, the distal bond site 120 constrains relative movement in one or more degrees of freedom between the associated portions of the floating sleeve 110 and the hypotube 130. For instance, the distal bond site 120 constrains relative distal movement of the distal portion of the hypotube 130 relative to the associated distal portion of the floating sleeve 110. In another example, the distal bond site 120 permits proximal relative movement of the distal portion of the hypotube 130 relative to the distal portion of the floating sleeve 110.

Although three bond sites are shown in FIG. 1 in other examples, one or more bond sites are used. For example, two bond sites are provided at various locations along the catheter body 102 with one or more associated floating segments for the floating sleeve 110. In another example, one bond site is provided along the catheter body 102 and the remainder of the floating sleeve 110 includes one or more floating segments.

The stagnation zones 126, 128, can be zones situated within the catheter assembly 100, such as proximal the bond sites 118, 120. In some cases, a portion of the hypotube 130 can be "solid" or have little to no openings for fluid to exit. The solid region can prevent fluid from exiting the lumen 132 of the hypotube in a proximal direction, and force the fluid to travel distally up the hypotube 130 to the spiral cut region 138 or the distal end of the hypotube 130 to exit the hypotube lumen 132 before exiting down the length of the catheter body 102.

For example, the catheter assembly 100 often will be primed or "flushed" prior to use. In this case, saline, or another flushing fluid, is run through the catheter to prime the device for use and ensure it is in good working order. When initial flushing is done, such flushing fluid exits through the distal end of the hypotube 130, or through the spiral cut region 138 of the hypotube 130 to escape the catheter body 102. If the hypotube 130 has a "solid" region without flow openings, this can cause fluid and air to be trapped in the lumen 132 of the hypotube 130, slowing inflation time. The air can become compressed, which can force fluid out of the catheter body 102 after flushing. Similarly, during deflation, such a solid region can cause difficulty clearing the fluid, as it must be moved distally first to exit the hypotube 130, then proximally to exit the catheter body 102.

However, the catheter assembly 100 include flow openings 134 to address this challenge. The flow openings 134 can be configured for movement of fluid through the hypotube 130 wall to the lumen 112 of the sleeve 110 and proximally down the catheter body, or conversely for more efficient flushing. The flow openings 134 are configured to reduce buildup of bubbles in the stagnation zone but allowing for release of fluid therethrough. The flow openings 134 are configured to encourage fluid flow in the stagnation zone. The flow openings 134 can be situated about one third of the way along the hypotube from the proximal portion.

The flow openings 134 can be small, each having a diameter of less than about 0.50 mm, 0.40 mm, 0.30 mm, 0.20 mm, or 0.10 mm. In some cases, the flow openings 134 can have circular cross-sections. In some cases, the flow openings 134 can have non-circular cross sections, such as oval, rectangular, triangular, diamond, or other cross-sections.

The balloon 146 is coupled to the distal portion 106 of the catheter body 102, and in fluid communication with the catheter assembly 100. The balloon 146 is actuatable between an expanded state and a collapsed state. When the balloon 146 is actuated between the expanded state and the collapsed state, the flow openings 134 are configured to expel fluid. During inflation of the balloon 146, the flow openings 134 allow fluid flow through between the lumen 132 of the hypotube 130 and the lumen 112 of the sleeve 110, to prevent stagnation. Similarly, during deflation of the balloon 146, the flow openings 134 allow fluid flow through between the lumen 132 of the hypotube 130 and the lumen 112 of the sleeve 110. The balloon 146 can have a length of about 10 mm to about 250 mm, and an inflated diameter of about 1 mm to about 10 mm.

The access port 144 shown in FIG. 1 is a rapid exchange port for easy access to the hypotube 130 when applying or inserting the catheter assembly 100 into a patient cavity or passageway. The access port 144 allows for easy removal of the hypotube 130 or other stiffening wire. Shown in FIG. 1, the hypotube 130 terminates in or near the access port 144, such that the hypotube 130 does not reach or interact with the balloon 146 or balloon protector 148. In some cases, an additional guide wire may be used in conjunction with the access port 144 for easier movement of the catheter assembly 100.

The balloon 146 is sheltered by the balloon protector 148 to prevent puncture of the balloon 146 prior to or during insertion. The balloon 146 and the balloon protector 148 are coupled with the distal floating hypotube segment 122 in or near the distal portion 106 of the catheter assembly 100. The sub-assembly includes support for the balloon 146 and balloon protector 148, and acts as an insertion tip for the catheter assembly 100. The balloon protector 148 can be removed after or during insertion.

Shown in more detail in FIG. 2, the catheter assembly 100 of FIG. 1 includes the hypotube 130, with a proximal portion 104 and a distal portion 106. The hypotube 130 may be, for example, a hypotube, a stiffening wire, a braid, coil, inner polymer liner, or the like that enhances pushability and resists buckling.

The hypotube 130 extends between the proximal portion 104 and the distal portion 106 of the catheter body 102 of the catheter assembly 100. The hypotube 130 is at least partially received within the floating sleeve 110, with optional clearance therebetween. As described herein, the hypotube 130 and the floating sleeve 110 are not bonded along the continuous length of the hypotube 130, such that the hypotube 130 and the floating sleeve 110 may "float" or move relative each other (e.g., along one or more floating segments). In some cases, the hypotube 130 is bonded to the floating sleeve 110 at distinct locations, such as one or more bond sites, and not continuously.

In one example, there is physical clearance between the hypotube 130 and the floating sleeve 110, or a "gap", that facilitates lateral and longitudinal movement therebetween. The clearance between them allows for sliding, moving, telescoping, and other motion between the hypotube 130 and the floating sleeve 110. For instance, a gap is provided therebetween and represented with variations in the sleeve inner diameter (larger) in comparison to the frame member outer diameter (smaller).

The gap can also allow for fluid flow between the hypotube 130 and the sleeve 110. The gap can be continuous, or broken up between the various bond sites 118, 120. The gap can be subject to fluid flow back-up, such as during flushing or priming of the catheter assembly 100. In some cases, the gap can be subject to bubble formation therein.

As shown in FIG. 2, the hypotube 130 has a spiral cut region 138 (e.g., scored, full penetration cut, perforations or the like having a helical, slanted or spiral configuration) along its length, from the distal portion 106 to the proximal portion 104. This enhances flexibility near the proximal portion 104 while at the same time maintaining specified rigidity and pushability near the distal portion 106. In one example, the spiral cut region 138 is continuous along the length of the hypotube 130. The spiral cut region 138 can provide a transition region between a more supported region and an unsupported region. In contrast, a non-spiral cut portion of the catheter assembly 100, such as at the floating segment 122, can be more rigid and supportive. The unsupported region towards the distal portion 106 can be more flexible than the proximal portion 104.

In some cases, the hypotube 130 includes a spiral cut region 138 that is a continuous cut around an external surface of the hypotube 130. In another example, the spiral cut includes a first pitch angle and second pitch angle, wherein the second pitch angle is lesser than the first pitch angle, or alternatively wherein the second pitch angle is larger than the first pitch angle. In some cases, the spiral cut region 138 gradually changes from the first pitch angle to the second pitch angle along the hypotube 130 from the distal portion 106 of the assembly to the proximal portion 104 of the assembly. The flow openings 134 can be situated on the hypotube 130 between the spiral cut region 138 and the proximal portion 104.

The end portion 145 and skive 139 resides on or near the distal portion 106 of the hypotube 130. With the hypotube 130 in the floating sleeve 110, the end portion 145 rests on or near the access port 144. The profile of the end portion 145 in some examples provides a stress riser during deflection of the catheter body 102.

Figure 4:
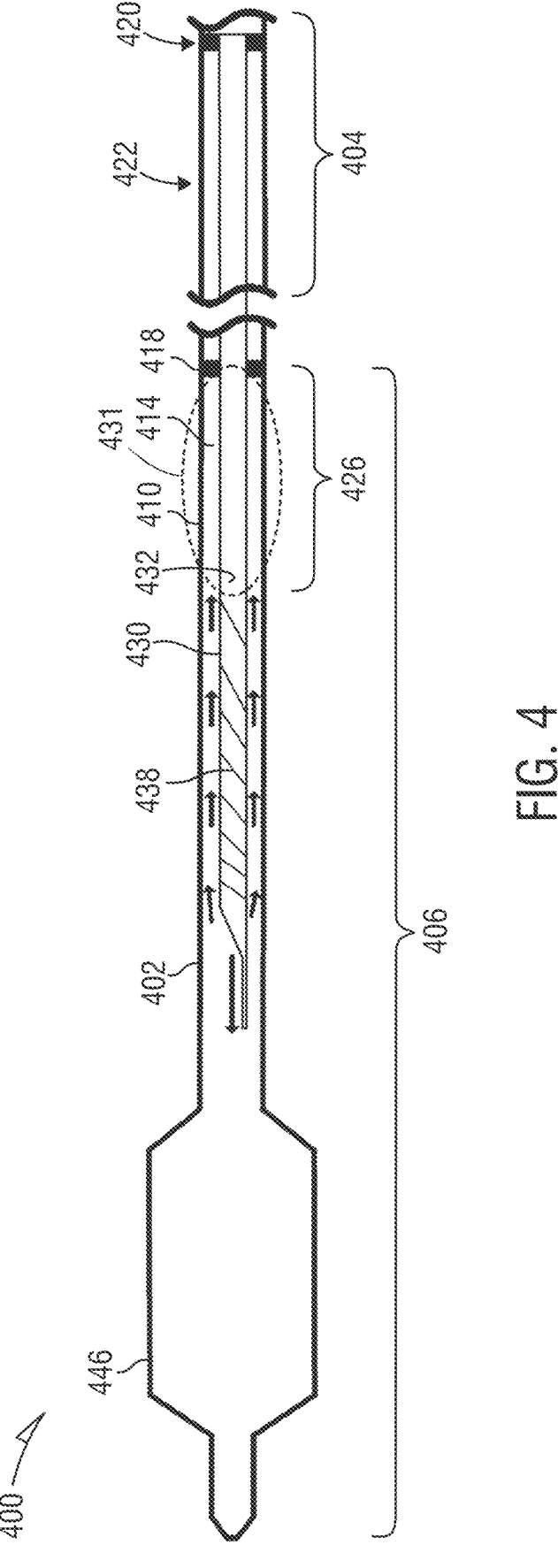
FIG. 4 is a side view of one example of a hypotube in a catheter assembly with fluid flow in a stagnation zone.

FIG. 4 illustrates a side view of one example of a hypotube in a catheter assembly 400 with fluid flow in a stagnation zone. The catheter assembly 400, similar to the catheter assembly 100 discussed above, includes a catheter body 402 extending between a proximal portion 404 and a distal portion 406. The catheter assembly 400 includes a hypotube 430, extending between the proximal portion 404 and the distal portion 406. The hypotube 430 extends through solid region 431 in a stagnation zone. The catheter assembly 400 further includes a sleeve 410 coupled around the hypotube 430 and extending between the proximal portion 404 and the distal portion 406. The sleeve 410 is spaced from the hypotube 430 by a floating gap 414. The catheter assembly 400 includes a balloon 446 connected to the distal portion 406 of the catheter body 402. The balloon 446 is configured to be inflated and deflated by movement of fluid through the catheter body 402.

But the catheter assembly 400 shown in FIG. 4 does not include flow openings on the hypotube 430. This can cause stagnation of fluid flow through the catheter assembly 400 during initial flushing (e.g., priming), and during other types of inflation or deflation of the catheter assembly 400.

For example, during initial flushing, fluid must exit through the distal portion 406 of the hypotube 430, or through the spiral cuts 438, which are past the solid region 431 of the hypotube 430. The solid region 431 of the hypotube 430, however, does not contain openings, slits, or other mechanisms through which fluid can exit the hypotube 430 lumen. For this reason, stagnation can often occur. For example, air in this solid region 431 can be trapped as the catheter body 402 is filled with fluid (such as saline or other priming fluid). This can slow inflation time of the catheter assembly 400. Air trapped in this solid region 431 can become compressed, forcing fluid out of the catheter body 402 after flushing.

Similarly, during deflation, the solid region 431 can be difficult to clear out, as fluid must be moved distally to reach an opening before being extracted proximally.

Figure 5:
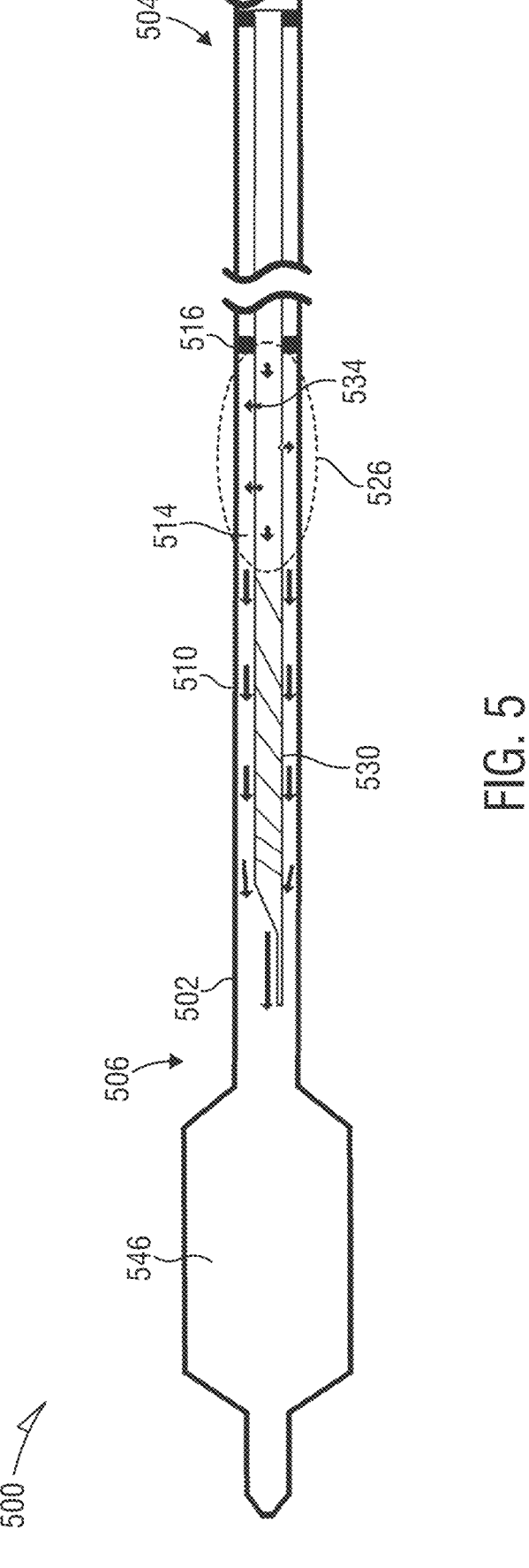
FIG. 5 is a side view of one example of a hypotube with flow openings in a catheter assembly with fluid flow in a stagnation zone.
Figure 6:
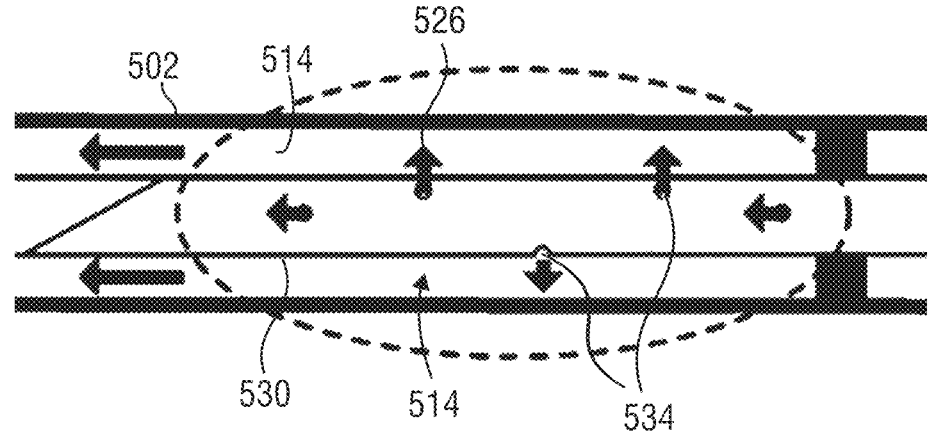
FIG. 6 is a close-up view of one example of flow openings in a hypotube.

By contrast, FIG. 5 illustrates a side view of one example of a hypotube with flow openings 534 in a catheter assembly 500 with fluid flow in a stagnation zone 526. FIG. 6 illustrates a close-up view of one example of flow openings 534 in a hypotube 530, such as the hypotube of FIG. 5. FIGS. 5 and 6 will be discussed together.

The example catheter assembly 500 includes a catheter body 502 extending between a proximal portion 504 and a distal portion 506. The catheter assembly 500 includes a hypotube 530, extending between the proximal portion 504 and the distal portion 506. The hypotube 530 includes a plurality of flow openings 534 situated in the hypotube 530 in a stagnation zone 526. The catheter assembly 500 further includes a sleeve 510 coupled around the hypotube 530 and extending between the proximal portion 504 and the distal portion 506. The sleeve 510 is spaced from the hypotube 530 by a floating gap 514. the plurality of flow openings 534 are configured to allow flow between the hypotube 530 and the floating gap 514 in the stagnation zone 526. The catheter assembly 500 includes a balloon 546 connected to the distal portion 506 of the catheter body 502. The balloon 546 is configured to be inflated and deflated by movement of fluid through the catheter body 502.

Stagnation can occur in the catheter assembly 500 during priming, flushing, or other movement of fluid through the catheter body 502. Stagnation can include blockage, bubbles, fluid buildup, or combinations thereof, in the floating gap 514. Stagnation can occur in fluid flow between the hypotube 530 and the sleeve 510, such as at floating segments near bond sites. For example, stagnation zone 526 can be prone to stagnation, which can interfere with function of the assembly.

The plurality of flow openings 534 allow for fluid flow with reduced stagnation and bubble formation during flushing or prepping of the catheter assembly 500, such as when fluid is used to prime or clean the catheter assembly 500.

For example, during initial flushing (e.g., priming of the catheter assembly 500), the plurality of flow openings 534 allow fluid added from the distal portion 506 of the hypotube 530 to fill the stagnation zone 526 (e.g., not having openings for fluid flow) of the hypotube 530 from a point just distal to the bond site 516.

Similarly, during deflation, the flow openings 534 can minimize the dead region, allowing fluid to be efficiently extracted from the distal portion 506 of the catheter body 502.

Additionally, the plurality of flow openings 534 allow for fluid flow through the stagnation zone 526 during inflation or deflation of the balloon 546. During inflation fluid flows from the hypotube 530 into the balloon 546 and expands the balloon 546. During inflation, the plurality of flow openings 534 relieve stagnation in the floating gap 514. During deflation, fluid flows from the balloon 546 out the hypotube 530, and during deflation the plurality of flow openings 534 relieve stagnation in the floating gap 514.

The plurality of flow openings 534 can be arranged around the hypotube 530, such as in a pattern to distribute stress around the hypotube 530. In some cases, the flow openings 534 can be arranged in a spiral pattern around the hypotube 530. In some cases, the flow openings 534 can be evenly spaced along or around the hypotube 530.

Figure 7:
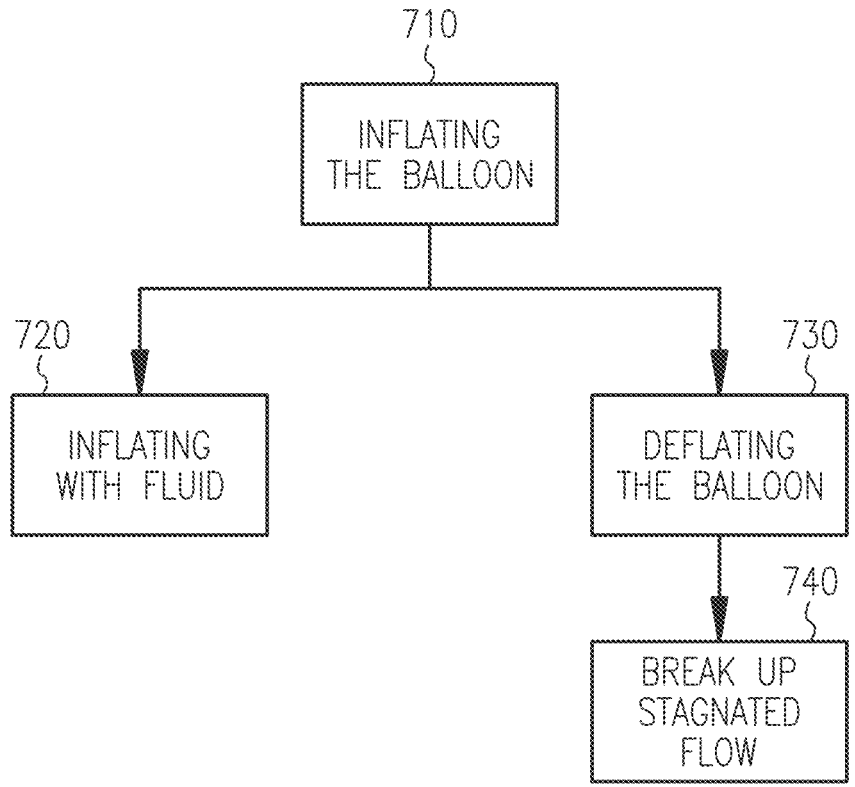
FIG. 7 is a flow chart depicting a method of evacuating fluid from a catheter assembly at a specified position.

FIG. 7 illustrates a method 700 of evacuating fluid from a catheter assembly at a specified position. The method 700 begins with inflating a balloon of the catheter assembly proximate to the specified position (710). The catheter assembly includes a hypotube, a sleeve coupled around the hypotube, and an inflatable balloon, wherein the hypotube and the sleeve are movable relative to each other.

Subsequently, the method includes inflating the balloon (720). Inflating the balloon includes draining fluid out of the hypotube via one or more flow openings on the hypotube. Next, the method includes deflating the balloon (730). Deflating the balloon includes draining fluid out of the hypotube via one or more flow openings in the hypotube.

Subsequently, the method includes breaking up stagnated flow between the hypotube and the sleeve by allowing fluid flow through the one or more openings (740). The method can optionally include breaking up bubbles between the hypotube and the sleeve by allowing fluid flow through the one or more openings. The method can optionally include navigating the catheter assembly along a passageway toward a specified position.

VARIOUS NOTES AND EXAMPLES

Example 1 can include catheter assembly, comprising a catheter body extending between a proximal portion and a distal portion. The catheter body can include a sleeve extending between the proximal and distal portions, wherein the sleeve includes a sleeve lumen; a hypotube having a hypotube lumen, the hypotube extends between the proximal and distal portions and is received within the sleeve lumen; at least one bond site connecting the sleeve to the hypotube; and a floating gap between the hypotube and the sleeve, the floating gap having a stagnation zone proximate the at least one bond site. The hypotube can include at least one flow opening extending from the hypotube lumen to the stagnation zone, and the at least one flow opening is configured to permit flow between the stagnation zone and the hypotube lumen.

Example 2 can include Example 1, wherein the flow opening is configured for movement of fluid therethrough.

Example 3 can include any of Examples 1-2, further comprising a balloon fluidly connected to the distal portion of the catheter body.

Example 4 can include any of Examples 1-3, wherein the balloon is actuatable between an expanded state and a collapsed state.

Example 5 can include any of Examples 1-4, wherein when the balloon is actuated between the expanded state and the collapsed state, the flow opening is configured to expel fluid.

Example 6 can include any of Examples 1-5, wherein the flow opening is configured to allowing fluid flow therethrough during inflation of the balloon.

Example 7 can include any of Examples 1-6, wherein the flow opening is configured to allowing fluid flow therethrough during deflation of the balloon.

Example 8 can include any of Examples 1-7, wherein the flow opening is configured to allowing fluid flow therethrough during priming of the assembly.

Example 9 can include any of Examples 1-8, wherein the flow opening is configured to reduce buildup of bubbles in the stagnation zone.

Example 10 can include any of Examples 1-9, wherein the flow opening is configured to encourage fluid flow in the stagnation zone.

Example 11 can include any of Examples 1-10, wherein the flow opening each comprise a diameter of less than about 0.20 mm.

Example 12 can include any of Examples 1-11, wherein the flow opening each comprise a circular cross-section.

Example 13 can include any of Examples 1-12, wherein the flow opening each comprise a non-circular cross-section.

Example 14 can include any of Examples 1-13, wherein the flow opening is situated about one third of the way along the hypotube from the proximal portion.

Example 15 can include any of Examples 1-14, wherein the hypotube comprises a spiral cut.

Example 16 can include any of Examples 1-15, wherein the spiral cut comprises a continuous cut around an external surface of the hypotube.

Example 17 can include any of Examples 1-16, wherein the spiral cut comprises a first pitch angle and second pitch angle.

Example 18 can include any of Examples 1-17, wherein the second pitch angle is lesser than the first pitch angle.

Example 19 can include any of Examples 1-18, wherein the second pitch angle is larger than the first pitch angle.

Example 20 can include any of Examples 1-19, wherein the spiral cut gradually changes from the first pitch angle to the second pitch angle along the hypotube from the distal portion of the assembly to the proximal portion of the assembly.

Example 21 can include any of Examples 1-20, wherein the flow opening is situated on the hypotube between spiral cut and the proximal portion.

Example 22 can include any of Examples 1-21, wherein the sleeve includes at least one floating segment and one or more bond sites along the catheter body, wherein the at least one floating segment of the sleeve is moveable relative to the hypotube, and wherein the one or more bond sites of the floating sleeve are interconnected with the hypotube.

Example 23 can include a catheter assembly comprising a catheter body extending between a proximal portion and a distal portion. The catheter body can include a hypotube extending between the proximal and distal portions, a plurality of flow openings on the hypotube, wherein the plurality of flow openings are situated on the hypotube in a stagnation zone; and a sleeve coupled around the hypotube and extending between the proximal and distal portions, the sleeve coupled to the hypotube by at least one bond site, wherein the sleeve is spaced from the hypotube by a floating gap. The plurality of flow openings can be configured to allow flow between the hypotube and the floating gap in the stagnation zone. The assembly can further include a balloon fluidly connected to the distal portion of the catheter body, the balloon configured to be inflated and deflated by movement of fluid through the catheter body, wherein the plurality of flow openings allow for fluid through the stagnation zone during inflation and deflation of the balloon.

Example 24 can include Example 23, wherein during inflation fluid flows from the hypotube into the balloon and expands the balloon, and wherein during inflation the plurality of flow openings relieve stagnation in the floating gap.

Example 25 can include any of Examples 23-24, wherein during deflation fluid flows from the balloon out the hypotube, and wherein during deflation the plurality of flow openings relieve stagnation in the floating gap.

Example 26 can include any of Examples 23-25, wherein stagnation comprises blockage, bubbles, fluid buildup, or combinations thereof, in the floating gap.

Example 27 can include a method of evacuating fluid from a catheter assembly comprising inflating a balloon of the catheter assembly proximate to a specified position, the catheter assembly including a hypotube, a sleeve coupled around the hypotube, and an inflatable balloon, wherein the hypotube and the sleeve are movable relative to each other, and inflating the balloon, wherein inflating the balloon comprises draining fluid out of the hypotube via one or more flow openings on the hypotube.

Example 28 can include Example 27, further comprising deflating the balloon, wherein deflating the balloon comprises draining fluid out of the hypotube via one or more flow openings in the hypotube.

Example 29 can include any of Examples 27-28, further comprising breaking up stagnated flow between the hypotube and the sleeve by allowing fluid flow through the one or more openings.

Example 30 can include any of Examples 27-29, further comprising breaking up bubbles between the hypotube and the sleeve by allowing fluid flow through the one or more openings.

Example 31 can include any of Examples 27-30, further comprising navigating the catheter assembly along a passageway toward a specified position.

Each of these non-limiting examples can stand on its own, or can be combined in various permutations or combinations with one or more of the other aspects.

The above description includes references to the accompanying drawings, which form a part of the detailed description. The drawings show, by way of illustration, specific embodiments in which the invention can be practiced. These embodiments are also referred to herein as "aspects" or "examples." Such aspects or example can include elements in addition to those shown or described. However, the present inventors also contemplate aspects or examples in which only those elements shown or described are provided. Moreover, the present inventors also contemplate aspects or examples using any combination or permutation of those elements shown or described (or one or more features thereof), either with respect to a particular aspects or examples (or one or more features thereof), or with respect to other Aspects (or one or more features thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described aspects or examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as aspects, examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A catheter assembly comprising:
   a catheter body extending between a proximal portion and a distal portion, the catheter body including:
      a sleeve extending between the proximal and distal portions, wherein the sleeve includes a sleeve lumen;
      a hypotube having a hypotube lumen, the hypotube extends between the proximal and distal portions and is received within the sleeve lumen;
      at least one bond site connecting the sleeve to the hypotube, wherein the hypotube and the sleeve are spaced forming a floating gap distal to the at least one bond site, and
         wherein the hypotube includes at least one flow opening extending from the hypotube lumen to the floating gap, and the at least one flow opening is configured to permit flow between the floating gap and the hypotube lumen;
         wherein the sleeve includes at least one floating segment and one or more bond sites along the catheter body, wherein the at least one floating segment of the sleeve is moveable relative to the hypotube, and the one or more bond sites of the floating sleeve are interconnected with the hypotube.

2. The catheter assembly of claim 1, further comprising a stagnation zone along at least a portion of the floating gap.

3. The catheter assembly of claim 1, wherein the floating gap is proximate the at least one bond site.

4. The catheter assembly of claim 1, wherein the at least one flow opening is positioned adjacent to the at least one bond site.

5. The catheter assembly of claim 1, wherein the at least one flow opening comprises a plurality of flow openings arranged in a spiral around the hypotube.

6. The catheter assembly of claim 1, wherein the at least one flow opening is configured for movement of fluid therethrough.

7. The catheter assembly of claim 1, further comprising a balloon fluidly connected to the distal portion of the catheter body.

8. The catheter assembly of claim 7, wherein the balloon is actuatable between an expanded state and a collapsed state.

9. The catheter assembly of claim 8, wherein when the balloon is actuated between the expanded state and the collapsed state, the least one flow opening is configured to expel fluid.

10. The catheter assembly of claim 7, wherein the at least one flow opening is configured to allowing fluid flow therethrough during inflation of the balloon.

11. The catheter assembly of claim 7, wherein the at least one flow opening is configured to allowing fluid flow therethrough during deflation of the balloon.

12. The catheter assembly of claim 7, wherein the at least one flow opening is configured to allowing fluid flow therethrough during priming of the assembly.

13. The catheter assembly of claim 1, wherein the at least one flow opening is configured to reduce buildup of bubbles in a stagnation zone.

14. The catheter assembly of claim 1, wherein the at least one flow opening is configured to encourage fluid flow in a stagnation zone.

15. The catheter assembly of claim 1, wherein the at least one flow opening each comprise a diameter of less than about 0.20 mm.

16. The catheter assembly of claim 1, wherein the at least one flow opening each comprise a circular cross-section.

17. The catheter assembly of claim 1, wherein the at least one flow opening each comprise a non-circular cross-section.

18. The catheter assembly of claim 1, wherein the at least one flow opening is situated about one third of the way along the hypotube from the proximal portion.

19. The catheter assembly of claim 1, wherein the hypotube comprises a spiral cut.

20. The catheter assembly of claim 19, wherein the spiral cut comprises a continuous cut around an external surface of the hypotube.

21. The catheter assembly of claim 19, wherein the spiral cut comprises a first pitch angle and second pitch angle.

22. The catheter assembly of claim 21, wherein the second pitch angle is lesser than the first pitch angle.

23. The catheter assembly of claim 21, wherein the second pitch angle is larger than the first pitch angle.

24. The catheter assembly of claim 21, wherein the spiral cut gradually changes from the first pitch angle to the second pitch angle along the hypotube from the distal portion of the assembly to the proximal portion of the assembly.

25. The catheter assembly of claim 21, wherein the at least one flow opening is situated on the hypotube between the spiral cut and the proximal portion.

26. A catheter assembly comprising:
a catheter body extending between a proximal portion and a distal portion, the catheter body including:
   a hypotube extending between the proximal and distal portions,
   a plurality of flow openings on the hypotube, wherein the plurality of flow openings are situated on the hypotube in a stagnation zone; and
   a sleeve coupled around the hypotube and extending between the proximal and distal portions, the sleeve coupled to the hypotube by at least one bond site, wherein the sleeve is spaced from the hypotube by a floating gap;
   wherein the plurality of flow openings are configured to allow flow between the hypotube and the floating gap in the stagnation zone;
   wherein the sleeve includes at least one floating segment and one or more bond sites along the catheter body, wherein the at least one floating segment of the sleeve is moveable relative to the hypotube, and the one or more bond sites of the floating sleeve are interconnected with the hypotube; and
a balloon fluidly connected to the distal portion of the catheter body, the balloon configured to be inflated and deflated by movement of fluid through the catheter body, wherein the plurality of flow openings allow for fluid through the stagnation zone during inflation and deflation of the balloon.

27. The catheter assembly of claim 26, wherein during inflation fluid flows from the hypotube into the balloon and expands the balloon, and wherein during inflation the plurality of flow openings relieve stagnation in the floating gap.

28. The catheter assembly of claim 26, wherein during deflation fluid flows from the balloon out the hypotube, and wherein during deflation the plurality of flow openings relieve stagnation in the floating gap.

29. The catheter assembly of claim 28, wherein stagnation comprises blockage, bubbles, fluid buildup, or combinations thereof, in the floating gap.

* * * * *